(12) United States Patent
Nazabal et al.

(10) Patent No.: US 8,323,983 B2
(45) Date of Patent: Dec. 4, 2012

(54) MASS SPECTROMETRIC ANALYSIS METHOD

(75) Inventors: Alexis Nazabal, Zürich (CH); Ryan Wenzel, Zürich (CH); Renato Zenobi, Zürich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 50 days.

(21) Appl. No.: 11/919,801

(22) PCT Filed: May 4, 2006

(86) PCT No.: PCT/CH2006/000245
§ 371 (c)(1),
(2), (4) Date: Nov. 27, 2007

(87) PCT Pub. No.: WO2006/116893
PCT Pub. Date: Nov. 9, 2006

(65) Prior Publication Data
US 2009/0263786 A1    Oct. 22, 2009

(30) Foreign Application Priority Data

May 4, 2005   (EP) .................................... 05405338

(51) Int. Cl.
*G01N 24/00* (2006.01)
*G01N 33/00* (2006.01)
*G01N 33/50* (2006.01)
*C12Q 1/70* (2006.01)
*C12Q 1/00* (2006.01)

(52) U.S. Cl. ................... 436/173; 436/86; 435/5; 435/4

(58) Field of Classification Search ................. 436/173, 436/86; 435/5, 4
See application file for complete search history.

(56) References Cited

U.S. PATENT DOCUMENTS

| 7,943,387 B2 * | 5/2011 | Nazabal et al. ................. 436/86 |
| 2004/0229369 A1 | 11/2004 | Kruppa et al. |

FOREIGN PATENT DOCUMENTS

| WO | 03/091273 | 11/2003 |
| WO | 2004/061422 | 7/2004 |

OTHER PUBLICATIONS

Farmer, T. B., Assessin gthe Multimeric States of Proteins: Studies Using Laser Desorption Mass Spectrometry, Biological Mass Spectrometry, vol. 20, 1991, pp. 796-800.*
J-L. Baneres et al., "Structure-based Analysis of GPCR Function: Evidence for a Novel Pentameric Assembly between the Dimeric Leukotriene $B_4$ Receptor BLT1 and the G-protein", J. Mol. Biol., vol. 329, pp. 815-829, Jun. 13, 2003.
A. Sinz, "Chemical Cross-linking and FTICR Mass Spectrometry for Protein Structure Characterization", Analytical and Bioanalytical Chemistry, vol. 381, No. 1, pp. 44-47, Jan. 2005.
A. Rostom et al., "Detection and Selective Dissociation of Intact Ribosomes in a Mass Spectrometer", PNAS, vol. 97, No. 10, pp. 5185-5190, May 9, 2000.
Z. Yu et al., "Structural Characterization of Human Hemoglobin Crosslinked by bis(3,5-dibromosalicyl) fumarate using mass spectrometric techniques", Protein Science, vol. 6, No. 12, pp. 2568-2577, 1997.

* cited by examiner

*Primary Examiner* — Christine T Mui
(74) *Attorney, Agent, or Firm* — Wenderoth, Lind & Ponack, L.L.P.

(57) ABSTRACT

Methods of using mass spectrometry and in particular matrix assisted laser desorption-ionization (MALDI) mass spectrometry to analyze, or otherwise detect the presence of or determine the identity of intact ions of undigested, unfragmented covalently stabilized supramolecular target-ligand-complexes, as well as the use of these methods in various biological application such as characterization of antibodies, drug discovery, and complexomics including automated or higher throughput applications.

9 Claims, 9 Drawing Sheets

A) NHS-Ester Reaction

B) Imidoester Reaction

MASS SPECTROMETRIC ANALYSIS METHOD

This application is a U.S. national stage of International Application No. PCT/CH2006/000245 filed May 4, 2006.

FIELD OF THE INVENTION

The present invention generally relates to methods of using mass spectrometry and in particular matrix assisted laser desorption-ionization (MALDI) mass spectrometry to analyze, or otherwise detect the presence of or determine the identity of intact ions from undigested, unfragmented covalently stabilized supramolecular target-ligand-complexes from multicomponent matrices.

The present invention also provides the use of these methods in various life sciences applications including but not limited to antibody characterization, drug screening and profiling applications in the frame of drug discovery as well as complexomics including automated or higher throughput applications.

BACKGROUND OF THE INVENTION

Identification and characterization of a broad range of non-covalent interactions between target molecules and their ligands, such as the biospecific interaction of proteins, or the interaction between a drugs and a particular binder protein,— is with growing significance in biochemistry research and drug discovery. Protein-protein interactions e.g. at a cellular level play a major role in signal transduction events, and consequently in cellular response to external stimuli and the pathophysiological alteration of diseased cells. Conventional technologies for a specific, direct detection of such non-covalent complexes include Western blot, whereby the protein extract is separated by gel electrophoresis, (Kemeny, D. M. and Challacombe, S. J. (eds.), in "ELISA and other Solid Phase Immunoassays"; John Wiley & Sons, Chichester (1988)), ELISA and Radioligand Binding Assays (Berson et al., Clin. Chim. Acta, 22:51-60 (1968); Chard, T. "An Introduction to Radioimmunoassay and Related Techniques," Elsevier Biomedical Press, Amsterdam, p 95-110 (1982)), Surface-Plasmon Resonance (Karlsson et al., J. Immunol. Methods, 145:229-240 (1991); Jonsson et al., Biotechniques, 11(5):620-627 (1991)), or Scintillation Proximity Assays (Udenfriend et al, Anal. Biochem., 161:494-500 (1987)). The radioligand binding assays are typically useful only when assessing the competitive binding of the unknown at the binding site for that of the radioligand and also require the use of radioactivity. The surface-plasmon resonance technique is a useful technology for measuring binding kinetics, and dissociation and association constants derived from such measurement are also helpful in elucidating the nature of the target-ligand interactions. However, all of these assays typically involve laborious and time-consuming experimentation or have to be performed by specifically educated individuals. All of these assays also require the user to know either the target molecule or the ligand prior to analysis because each require some type of preparation (i.e. label or immobilization) of the target or ligand molecule.

In recent years applications of mass spectrometry in the biosciences have been reported (Meth. Enzymol., Vol. 193, Mass Spectrometry (McCloskey, ed.; Academic Press, NY 1990); McLaffery et al., Acc. Chem. Res. 27:297-386 (1994); Chait and Kent, Science 257:1885-1894 (1992); Siuzdak, Proc. Natl. Acad. Sci., USA 91:11290-11297 (1994)), including methods for mass spectrometric analysis of biopolymers (Hillenkamp et al. (1991) Anal. Chem. 63:1193A-1202A; US 2004/0229369A1;U.S. Pat. No. 6,558,902). The so-called "soft ionization" mass spectrometric methods, including Matrix-Assisted Laser Desorption/Ionization (MALDI) and ElectroSpray Ionization (ESI), allow intact ionization, detection and mass determination of large molecules, i.e., well exceeding 300 kDa in mass (Fenn et al., Science 246:64-71 (1989); Karas and Hillenkamp, Anal. Chem. 60:2299-3001 (1988)).

Both MALDI mass spectrometry (MALDI-MS; reviewed in Nordhoff et al., Mass Spectrom. Rev. 15:67-138 (1997)) and ESI-MS have been used to analyze non-covalent protein complexes (Cohen et al, J. Am. Soc. Mass Spectrom. 8:1046-1052 (1997); Rosinke et al, J. Mass. Spec 30:1462-1468 (1995); Schar, M. Chimia 51:782-785 (1997); Woods et al. Anal. Chem. 67:4462-4465 (1995); Tito et al, Biophysical Journal 81:3503-3509 (2001); U.S. Pat. No. 6,329,146). Yet, for the study of undigested, unfragmented protein complexes by mass spectrometry, the sample preparation protocols and the instrument setup need to be adapted for each protein complexes targeted. Finding the favourable conditions to observe intact ions from protein complexes is time consuming and still a major difficulty to making these measurements routine in order to bring these studies from one-at-a-time to higher throughput. For MALDI MS, in order to detect non-covalent complexes special conditions, such as matrices solutions without organic solvent or soft laser analysis (i.e. first shot analysis) have to be determined. (Farmer and Caprioli, *J. Mass Spectrom.*, (1998); Zehl and Allmaier, *Rapid Commun. Mass Spectrom.*, (2003); Cohen, et al., *JASMS*, (1997)) Furthermore, most of these studies suffer from low signal intensities compared to those of the individual component due to instability of these non-covalent complexes and ease of dissociation during sample preparation and complex ionization.

There are very limited studies on intact undigested, unfragmented complexes by mass spectrometry. Furthermore, the study of crosslinked intact protein complexes is restricted to the analysis of homo-multimeric complex. These particular complexes naturally minimize analytical problems related with ion detection using MALDI MS, such as competition for ionization in the desorption plume or detector saturation decreasing detection of the complexes because of low mass ions. Yet, such homo-multimeric protein complexes are still a biological exception and the method has not been applied to other relevant biological complexes (T. B. Farmer, R. M. Caprioli, *Biol Mass Spectrom* 20, 796 (December, 1991)).

On the other hand, the study of digested protein complexes is an efficient yet indirect way to detect non-covalent protein complexes (Parker, C. E. and Tomer K. B, Molecular Biotechnology 20:49-62 (2002); WO 2002/058533A2). The method, is restricted by the selective desorption/ionization phenomenon and by the overlapping phenomenon due to the complexity of the peptide mixture obtained after proteolysis of the protein complexes. Also, because the spectra are an analysis of many peptide fragments of the complex it often takes complicated computer software in order to interpret the spectra. Sometimes in order to aid in identification of the peptide fragments, molecular tags are linked to the complex (US 2005/0095654A1; EP 0 850 320 B1; EP 1 150 120 A2; U.S. Pat. No. 6,635,452)

Clearly although the techniques referenced above show some degree of utility in performing certain types of general analyses, shortcomings in high sensitivity, ease of operation or understanding, and analytical compatibility remain.

Thus, there is a need for the development of robust, accurate, sensitive and reliable methods to routinely detect and analyze intact ions from undigested, unfragmented supramolecular target-ligand-complexes from both purified multicomponent samples or heterogeneous biological matrices, which will overcome the above shortcomings.

Applicants have now discovered methods to analyse the presence or the identity of intact ions of undigested, unfragmented supramolecular target-ligand-complexes from either purified multicomponent mixtures or heterogeneous biological matrices with high sensitivity and accuracy using mass spectrometry, in particular MALDI ToF mass spectrometry using sensitive high mass detection for a robust and routine analysis.

In particular the methods of the present application allow the analysis of intact non-covalent interactions between a target molecule and its ligand with high sensitivity and accuracy by first crosslinking the non-covalently bound target-ligand-complex and subsequently subjecting it to mass spectrometry, in particular MALDI ToF mass spectrometry using sensitive high mass detection with no digestion or fragmentation step.

The use of the methods of the present invention allows not only a direct mass analysis, but also the determination of the specific binding of a target molecule with its binding ligand, the site(s) of interaction between ligand and target and the relative binding affinity of ligand for the target.

The present application further provides the use of these methods as a very versatile tool in various biological applications such as characterization of antibodies, drug discovery, and complexomics, including automated or higher throughput applications.

SUMMARY OF THE INVENTION

It is an object of the present invention to provide methods to analyze, or otherwise detect the presence of or determine the identity of covalently stabilized supramolecular target-ligand-complexes from either purified multicomponent samples or heterogeneous biological matrices without digestion or fragmentation of the sample using mass spectrometry (MS).

In particular, the present invention provides methods for analyzing intact ions of undigested, unfragmented supramolecular target-ligand-complexes using mass spectrometry comprising the steps of:
  a) contacting a non-covalently bonded, supramolecular target-ligand-complex with a crosslinking reagent to form a covalently stabilized supramolecular target-ligand-complex, and
  b) analyzing the intact ions from the covalently stabilized supramolecular target-ligand-complex by mass spectrometry.

In a specific embodiment the supramolecular target-ligand-complex is analyzed from either purified multicomponent samples or heterogeneous biological matrices with no digestion or fragmentation step.

In a further specific embodiment, the supramolecular target-ligand-complex represents a complex of a target molecule with its ligand, where said target molecule and/or the ligand can be one particular or a plurality of proteins (e.g. antibody, receptor or enzyme), nucleic acids, synthetic organic compounds (e.g. drugs, polymers) or particles (e.g. viral particles) and the like. Thus, the complexes formed result from, protein-drug, protein-nucleic acid, protein-viral particles, or protein-protein-interactions, e.g. antibody-antigen, enzyme-substrate interactions, and the like.

It is a further object of the invention to use the methods of the present invention in various biochemistry and molecular/cell biology applications such as biochemical characterization of antibody-antigen interactions (e.g. antibody screening, epitope mapping, reaction kinetics), cellular signaling pathway mapping, as well as in drug discovery applications such as drug screening (e.g. direct target fishing using a bait protein or in competition assays), in vitro drug binding assays, drug profiling via mapping protein-protein interactions upon applying stress, as well as complexomics including automated and higher throughput applications.

These objects and their advantageous embodiments of the invention are achieved by a method with the features of the appended claims.

The methods of the present invention provide for a direct mass analysis of a complex of a target molecule with its binding ligand with no digestion or fragmentation, and thus they also include the ability to recognize variants of target molecules, to elucidate their nature, and the capability to analyze for, and identify, various ligands interacting with target molecules.

The invention itself will best be understood from the following description of the preferred embodiments of the present invention. It is understood that those skilled in the art may conceive modifications and/or variations to the specific embodiments shown and described herein. Any such modifications or variations that fall within the purview of this description are intended to be included therein as well. The description of preferred embodiments and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiments demonstrate the principles of the invention and its practical applications and enable others skilled in the art to best utilize the invention in various embodiments and with various modifications as are suited to the particular use contemplated.

DETAILED DESCRIPTION OF THE INVENTION

All patents, patent applications and publications cited herein are incorporated herein by reference. The meaning of certain terms and phrases used in the specification and claims are provided below. Unless defined otherwise, all technical and scientific terms used herein have the same meaning as is commonly understood by one of skill in the art to which the subject matter belongs.

The methods of the present invention allow the detection, identification or characterization of intact ions of undigested, unfragmented supramolecular target-ligand-complexes, e.g. from either purified multicomponent sample or heterogeneous biological matrices, using mass spectrometry.

Figure 1:
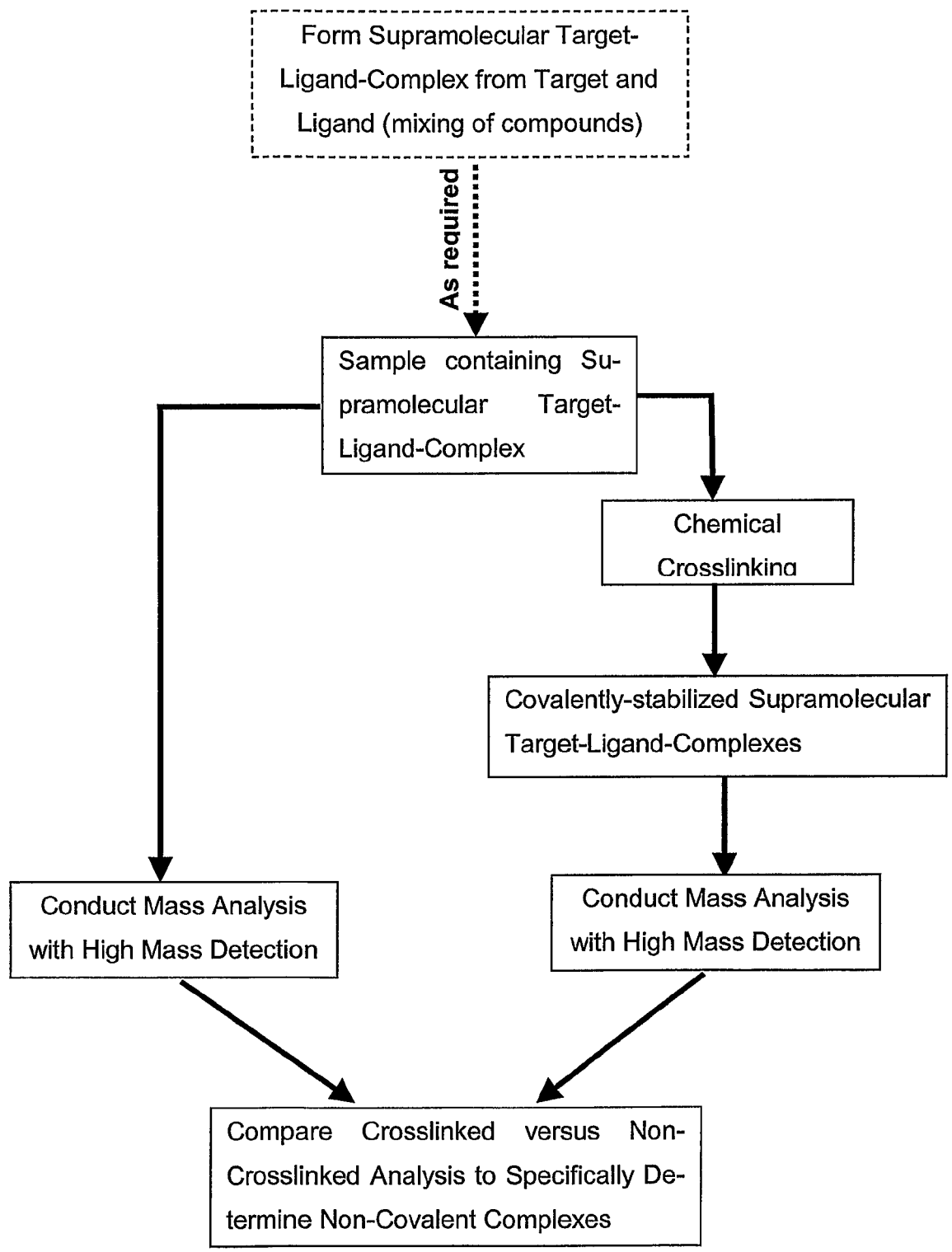
FIG. 1: Basic overview of method for analysis of supramolecular target-ligand-complexes by mass spectrometry according to the invention.

A box diagram describing a basic overview of the methods of invention for analysis of supramolecular target-ligand-complexes by mass spectrometry is shown in FIG. 1.

The methods of the present invention are based on the finding that upon stabilization of the non-covalently formed, supramolecular target-ligand-complexes by crosslinking, e.g. in either purified multicomponent sample or heterogeneous biological matrices, mass spectrometric analysis of these ions can be performed without digestion or fragmentation while they are held intact. Thus, the present invention provides methods for analyzing intact ions of undigested, unfragmented supramolecular target-ligand-complexes using mass spectrometry comprising the steps of:
  a) contacting a non-covalently bonded, supramolecular target-ligand-complex with a crosslinking reagent to form a covalently stabilized supramolecular target-ligand-complex, and
  b) analyzing the intact ions from the covalently stabilized supramolecular target-ligand-complex by mass spectrometry.

In a specific embodiment the supramolecular target-ligand-complex is analyzed from either purified multicomponent samples or heterogeneous biological matrices.

As used herein, the term "supramolecular target-ligand-complexes" refers to complexes arising from the specific binding of a target molecule with its binding ligand, wherein said target molecule and/or binding ligand can be one particular or a plurality of proteins (e.g. antibody, receptor or enzyme), nucleic acids, synthetic organic compounds (e.g. drugs, polymers) or particles (e.g. viral particles) and the like, to form said supramolecular target-ligand-complexes, such as protein-protein, protein-nucleic acid, protein-drug, protein-viral particles, antibody-antigen, substrate-enzyme complexes and the like.

As used herein, the term "intact ions" refers to charged molecules created for mass analysis from the covalently stabilized supramolecular target-ligand-complexes without proteolysis, degradation, or dissociation of the supramolecular target-ligand-complexes, before or during mass analysis.

As used herein, the term "covalently stabilized supramolecular target-ligand-complexes" refers to complexes as defined above, which have been crosslinked by any known (e.g. FIG. 2) and so far undiscovered means without disturbing the spatial arrangement of the complexes.

As used herein, the term "digested" refers to processes of disintegrating a molecule into smaller components, for example using proteases such as trypsin to digest a protein or protein complex into its peptide subunits.

As used herein, the term "fragmented" refers to processes of disintegrating a molecule into smaller components, for example using a collision cell within a mass spectrometer to fragment a protein or protein complex into its peptide subunits.

As used herein, the term "target" or "target molecule" refers to a higher mass molecule, which typically may be found in a biological source but may also be a synthetic molecule that is based on or derived from a naturally occurring molecule, and in particular includes proteins (both antibody and non-antibody proteins), polypeptides, glycopolypeptides, phosphopolypeptides, peptidoglycans, polysaccharides, peptidomimetics, lipids, carbohydrates, polynucleotides and other naturally occurring or synthetic macromolecules, preferably proteins, polypeptides, polysaccharides, peptidomimetics, lipids, carbohydrates, polynucleotides, more preferably proteins, polypeptides, peptidomimetics, polynucleotides. A target can be derived from a natural source or chemically synthesized.

As used herein, the term "ligand" (or "binding ligand") refers to a molecule that can specifically bind to its target, such as an antigen to an antibody, a substrate to an enzyme, a polypeptide to an epitope, a protein to a protein or to a group of proteins. The molecules described as ligand and target can be used interchangeably. Thus a ligand can be essentially any type of molecule such as a small molecule drug, peptide or polypeptide, protein, nucleic acid or oligonucleotide, carbohydrate such as oligosaccharides, viral particles, or any other small organic derived compound and synthetic macromolecule. A ligand can be derived from a natural source or chemically synthesized.

As used herein, the term "purified multicomponent sample" refers to any sample containing a heterogeneous or homogeneous mixture of proteins, polypeptides, glycopolypeptides, phosphopolypeptides, peptidoglycans, polysaccharides, peptidomimetics, lipids, carbohydrates, polynucleotides or organic compounds, which has been purified in part or completely.

As used herein, the term "heterogeneous biological matrices" refers to any crude reaction mixtures including mixtures obtained from dissolution of a solid material such as a tissue, cells, or a cell pellet; biological fluid such as urine, blood, saliva, amniotic fluid, or an exudate from a region of infection or inflammation; a cell extract, or biopsy sample; or mixtures obtained from a living source, for example, an animal such as a human or other mammal, a plant, a bacterium, a fungus or a virus.

The above defined terms "purified multicomponent sample" and "heterogeneous biological matrices" may also refer to synthetically obtained mixtures whereby a series of potential binding ligands is contacted with the target molecule.

As used herein, the term "specifically" or "interacts specifically" means that the binding interaction is detectable over non-specific interactions by a quantifiable assay.

As used herein, the term "high or higher mass" with reference to targets and their complexes with ligands refer to targets and their complexes with ligands that are larger than about 5 kDa, e.g. ranging from about 5 kDa to about 100 MDa, more specifically from about 50 kDa to about 50 MDa, most preferably from about 100 kDa to about 10 Mda.

As used herein, the term "analyze" means to identify or detect the presence, absence or change of, or determine the identity of such covalently stabilized supramolecular target-ligand-complexes as intact ions.

As used herein, the term "higher throughput" means to conduct more than one analysis per day, more specifically several per day, most preferably hundreds per day.

The methods of the present invention are in particular very useful as they allow mass resolution of both purified or crude samples, i.e. biological samples, which may or may not have undergone some purification but still may contain extraneous contaminants, with high accuracy, high sensitivity and high signal-to-noise ratio. Thus the methods of the present invention are able to clearly resolve the complexes, which may not be present in significant quantities, from the contaminant materials.

Thus mass analysis of high molecular weight covalently stabilized complexes from biological samples, which is otherwise difficult to analyze due to the presence of mixtures, contaminants, or impurities is made possible by the methods of the present invention and further may be made amenable to automation as desired in large-scale processes. This may include the use of software for analysis, detection and/or interpretation of the data as well as robotics for the control of the sample preparation and/or analysis.

Figure 2:
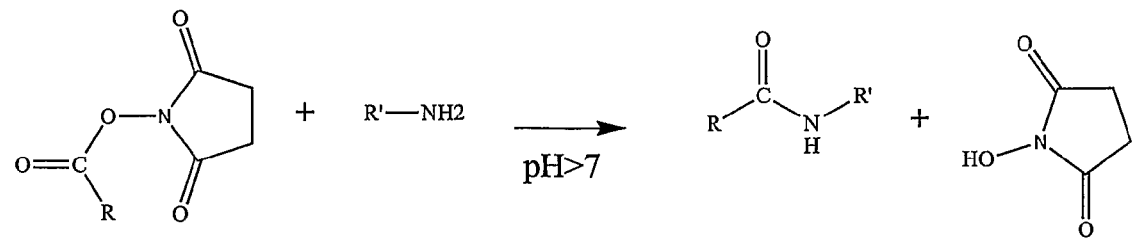
FIG. 2: Typical standard amine reactive crosslinking chemical reactions to be used for stabilizing non-covalent complexes prior to mass spectrometric analysis.
Figure 2:
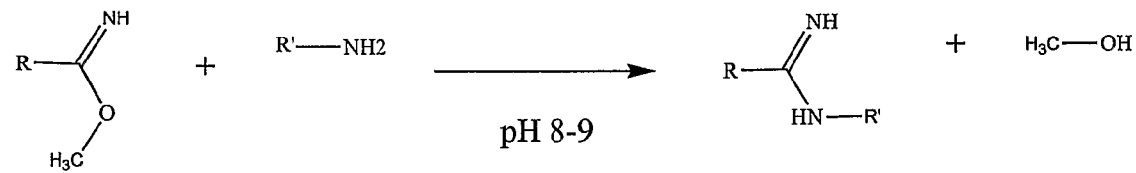

In practicing an embodiment of the method of the present invention, a sample containing the non-covalently bonded target-ligand-complex to be analysed is first subjected to crosslinking conditions using known or new crosslinking chemistry, such as for example standard amine reactive crosslinking chemical reactions to be used for stabilizing non-covalent complexes prior to mass spectrometric analysis as shown in FIG. 2. Typically, a solution containing a crosslinking reagent of choice was added to a sample containing the complex followed by incubation for a specified time, e.g. 30 minutes, to ensure completion of the reaction. Typical crosslinkers include reagents specific for a wide variety of reactive groups including but not limited to amines, carbohydrates, carboxyls, hydroxyls, and sulfhydryls, as well as reagents that react non-specifically or are photolabile and are well known in the art (see, for example, Wong, Chemistry of Protein Conjugation and Cross-Linking (CRC Press 1991); Hermanson, Bioconjugate Techniques (Academic Press 1996)). Possible crosslinking agents include both homo- and heteromultifunctional crosslinking agents and include imidoesters, N-hydroxysuccinimide-Esters (NHS-Esters), maleimides, haloacetyls, pyridyl disulfides, hydrazides, carbodiimides, aryl azides, Isocyanate, vinyl sulfones and the like. Common homobifunctional reagents that can be used include, e.g., Alpha-1-acid glycoprotein, (3-[(2-Aminoethyl) dithio]propionic acid.HCl), (Bis-[β-(4-Azidosalicylamido) ethyl]disulfide, (1,4-bis-Maleimidobutane), (1,4-bis-Maleimidyl-2,3-dihydroxybutane), (Bis-Maleimidohexane), (Bis-Maleimidoethane), (1,8-Bis-Maleimidodiethyleneglycol), (1,11-Bis-Maleimidotriethyleneglycol), (Bis[sulfosuccinimidyl]suberate), (Bis[2-(succinimidooxycarbonyloxy)ethyl] sulfone), (1,5-Difluoro-2,4-dinitrobenzene), (Dimethyl adipimidate.2HCl), (Dimethyl pimelimidate.2HCl), (Dimethyl Suberimidate.2HCl), (1,4-Di-[3'-(2'-pyridyldithio)propionamido]butane), (Disuccinimidyl glutarate), (Dithio-bis[succinimidylpropionate]), (Disuccinimidyl suberate), (Disuccinimidyl tartarate), (Dimethyl 3,3'-dithiobispropionimidate.2HCl), (Dithio-bis-maleimidoethane), (3,3'-Dithiobis[sulfosuccinimidylpropionate], (Ethylene glycol bis[succinimidylsuccinate]), (1,6-Hexane-bis-vinylsulfone), (Ethylene glycol bis [sulfosuccinimidylsuccinate]).(p-Azidobenzoyl hydrazide), N-(a-Maleimidoacetoxy) succinimide ester), (N-5-Azido-2-nitrobenzoyloxysuccinimide), (N-[4-(p-Azidosalicylamido) butyl]-3'-(2'-pyridyldithio)propionamide), (4-[p-Azidosalicylamido]butylamine), (N-β-Maleimidopropionic acid), (N-[β-Maleimidopropionic acid]hydrazide.TFA), (N-[b-Maleimidopropyloxy]succinimide ester), (1-Ethyl-3-[3-dimethylaminopropyl]carbodiimide Hydrochloride), (N-e-Maleimidocaproic acid), ([N-e-Maleimidocaproic acid] hydrazide), ([N-e-Maleimidocaproyloxy]succinimide ester), (N-k-Maleimidoundecanoic acid), (N-[k-Maleimidoundecanoic acid]hydrazide), (N-[g-Maleimidobutyryloxy]succinimide ester), (Succinimidyl 4-[N-maleimidomethyl]cyclohexane-1-carboxy-[6-amidocaproate]), (Succinimidyl 6-(3-[2-pyridyldithio]-propionamido)hexanoate), (m-Maleimidobenzoyl-N-hydroxysuccinimide ester), 4-(4-N-Maleimidophenyl)butyric acid hydrazide hydrochloride, (Methyl N-succinimidyl adipate), (N-Hydroxysuccinimidyl-4-azidosalicylic acid), (3-(2-Pyridyldithio)propionyl hydrazide), (N-[p-Maleimidophenyl]isocyanate), (N-Succinimidyl(4-azidophenyl)-1,3'-dithiopropionate), (N-Succinimidyl-6-[4'-azido-2'-nitrophenylamino]hexanoate) (N-Sulfosuccinimidyl-6-[4'-azido-2'-nitrophenylamino]hexanoate), (N-Succinimidyl-S-acetylthioacetate), (N-Succinimidyl-S-acetylthiopropionate), (Succinimidyl 3-[bromoacetamido]propionate), (N-Succinimidyl iodoacetate), (N-Succinimidyl[4-iodoacetyl]aminobenzoate), (Succinimidyl 4-[N-maleimidomethyl]cyclohexane-1-carboxylate), (Succinimidyl 4-[p-maleimidophenyl]butyrate), (Succinimidyl-6-[β-maleimidopropionamido]hexanoate), (4-Succinimidyloxycarbonyl-methyl-a-[2-pyridyldithio]toluene), (N-Succinimidyl 3-[2-pyridyldithio]-propionamido), ([N-e-Maleimidocaproyloxy]sulfosuccinimide ester), (N-[g-Maleimidobutyryloxy]sulfosuccinimide ester), (N-Hydroxysulfosuccinimidyl-4-azidobenzoate), (N-[k-Maleimidoundecanoyloxy]sulfosuccinimide ester), (Sulfosuccinimidyl 6(3-[2-pyridyldithio]-propionamido) hexanoate), (m-Maleimidobenzoyl-N-hydroxysulfosuccinimide ester), (Sulfosuccinimidyl[4-azidosalicylamido]-hexanoate), (N-Sulfosuccinimidyl(4-azidophenyl)-1,3'-dithiopropionate, Sulfo-SAED (Sulfosuccinimidyl 2-[7-amino-4-methylcoumarin-3-acetamido]ethyl-1, 3'dithiopropionate), Sulfo-SAND (Sulfosuccinimidyl 2[m-azido-o-nitrobenzamido]-ethyl-1,3'-dithiopropionate), Sulfo-SASD (Sulfosuccinimidyl-2-[p-azidosalicylamido] ethyl-1,3'-dithiopropionate), Sulfo-SFAD (Sulfosuccinimidyl-[perfluoroazidobenzamido]ethyl-1,3'-dithiopropionate), (N-Sulfosuccinimidyl[4-iodoacetyl]aminobenzoate), (Succinimidyl 4-[N-maleimidomethyl]cyclohexane-1-carboxylate), (Sulfosuccinimidyl 4-[p-maleimidophenyl]butyrate), (4-Sulfosuccinimidyl-6-methyl-a-(2-pyridyldithio) toluamido]hexanoate)), (N-[e-Trifluoroacetylcaproyloxy] succinimide ester) (sulfosuccinimidyl-2-[6-(biotinamido)-2-(p-azidobenzamido) hexanoamido]ethyl-1,3'-dithiopropionate), (β-[Tris(hydroxymethyl)phosphino] propionic acid (betaine), (Tris[2-maleimidoethyl]amine), (Tris-succinimidyl aminotriacetate). The target-ligand-complex can also conveniently be crosslinked using formaldehyde, glutaraldehyde, or glyoxal. Preferably, homobifunctional amine reactive crosslinkers, e.g., (Ethylene glycol bis

[succinimidylsuccinate]), (Ethylene glycol bis[sulfosuccinimidylsuccinate]), (Bis[2(succinimidooxycarbonyloxy)ethyl]sulfone), (Dithiobis[succinimidylpropionate]), (3,3'-Dithiobis[sulfosuccinimidylpropionate], (Dimethyl 3,3'-dithiobispropionimidate.2HCl), (Disuccinimidyl suberate), (Bis[sulfosuccinimidyl]suberate), (Dimethyl Suberimidate.2HCl), (Dimethyl pimelimidate.2HCl), (Dimethyl adipimidate.2HCl), (Disuccinimidyl glutarate), (Methyl N-succinimidyl adipate), (Disuccinimidyl tartarate) (1,5-Difluoro-2,4-dinitrobenzene). Most preferably, a mixture of two or more different crosslinkers that have been shown to have compatibility with mass spectrometric analysis. Multifunctional crosslinkers could also be used as purification tags for selectively removing crosslinked products from heterogeneous biological matrices or other complex solutions.

After completion of the crosslinking reaction, the liquid is intended to be used in any MS setup, preferably a MALDI MS setup. In a preferred embodiment, an aliquot, e.g. 1 microliter, of the sample containing the now covalently stabilized complex was mixed with an aliquot, e.g. 1 microliter, of a matrix solution to obtain a sample/matrix-mixture or spotted directly on a plate covered with a thin layer of matrix or other MALDI sample deposition techniques, as known by those familiar in the art. Typical matrix solutions for use in the methods disclosed herein have a sufficient absorption at the wavelength of the laser to be used in performing desorption and ionization and are a liquid at room temperature (20° C.) and can form a vitreous or glass solid. Among the preferred matrices are substituted or unsubstituted (1) alcohols, including glycerol, sugars, polysaccharides, 1,2-propanediol, 1,3-propanediol, 1,2-butanediol, 1,3-butanediol, 1,4-butanediol and triethanolamine; (2) carboxylic acids, including formic acid, lactic acid, acetic acid, propionic acid, butanoic acid, pentanoic acid and hexanoic acid, or esters thereof; (3) primary or secondary amides, including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitriles, hydrazine and hydrazide; and (6) alpha-cyano-cinamic acid, sinapinic acid. Materials of relatively low volatility are preferred to avoid rapid evaporation under conditions of vacuum during MS analyses. Preferably the liquid has an appropriate viscosity to facilitate dispensing of microliter to nanoliter volumes of matrix, either alone or mixed with a sample solution. Mixtures of different liquid matrices and additives to such matrices may be desirable to confer one or more of the properties described above. Preferably, any liquid(s) used in preparation of the solution are removed by drying the sample/matrix-mixture before analysis to form a homogenous "solid solution", i.e. comprising the analyte complexes distributed throughout the matrix. In a preferred embodiment, the matrix solution contains for example sinapinic acid (10 mg/mL) in a solution containing 7:3:1 of acetonitrile:water:0.1% trifluoroacetic acid (TFA). Due to the stabilization achieved by the crosslinking step it is not necessary to undergo the laborious process of optimizing "soft" conditions such as matrices solutions without organic solvent or soft laser analysis (i.e. low laser powers used or first shot analysis).

While the above described preferred embodiment involves using dried liquid solutions, other methods such as liquid MALDI, online AP-MALDI, solid phase preparation, and other sample preparation techniques could be used as they are well known in the art.

A sample/matrix-mixture to be analyzed by MS as disclosed herein generally contains the complex and the liquid matrix in a ratio of about 20 femtomol to 5 picomol of the complex to be analyzed.

Subsequently an aliquot of the resulting sample/matrix-mixture to be subjected to MALDI MS, e.g. 1 microliter, is deposited as a thin layer on a substrate.

While a vacuum Matrix Assisted Laser Desorption/Ionization (MALDI) is the preferred ionization technique, Electrospray Ionization (ESI) as well as other types of ionization for mass spectrometry, such as Atmospheric Pressure Chemical Ionization (APCI), Atmospheric Pressure MALDI (APM-ALDI), Chemical Ionization (CI), Fast Atom Bombardment (FAB), Secondary Ion Mass Spectrometry (SIMS), Electron Impact (EI), Field Desorption (FD) and Ionization (FI) or any other ionization source may be used, as they are well known in the art.

In a preferred embodiment, the ion particles generated are extracted for analysis by the mass analyzer in a delayed fashion prior to separation and detection in a mass analyzer. Preferably, the separation formats include, but are not limited to, linear or reflectron time-of-flight (ToF), with linear and nonlinear fields, for example, curved field reflectron; single or multiple quadrupole; single or multiple magnetic or electric sector; Fourier transform ion cyclotron resonance (FTICR); or ion trap mass spectrometers, most preferably, linear Time of Flight (ToF).

While a Superconducting Tunnel Junction (STJ) detector is preferred, other known detectors which are sensitive to high mass ions and thus are able to detect chemically stabilized multicomponent ions, which include, but are not limited to, Ion Conversion Dynode (ICD) detectors, optically decoupled, amplified, or specially coated electron multipliers or MCP's, and other cryodetectors or sensitive high mass detector may be used, as they are well known in the art.

While noncovalent interactions can be discerned from the individual spectra obtained according to the methods of the present invention, a direct comparison from crosslinked to uncrosslinked interactions allows a more precise analysis which is typically done using differential display. Differential analysis and analysis of multiple samples may also be aided by the use of sample handling robotics and/or analysis software.

The methods disclosed herein are also suitable for analyzing one or more complexes including a large number of complexes, for example in MALDI-MS, by depositing a plurality of sample compositions, each containing one or more covalently stabilized complexes, on a solid support, for example, a chip, in the form of an array. The analysis could include the detection of multiple complexes in one sample, the analysis of multiple components or combination of components within the same sample, or the analysis of multiple samples in an array form. It is understood that this can be applied in analogy to other masspectrometric analyzers and adapted to their specific setup. Additionally, the samples are originally in solution, require very small volumes (microliter) for analysis, and are sufficiently stabile once crosslinked. Thus, the methods disclosed herein are readily adaptable to automated or higher throughput assay formats.

Furthermore, the methods disclosed herein may provide an important tool in various analytical applications which are of great importance in drug development and diagnostics. These analytical applications include characterization of the antibody-antigen interactions with special regard to the specificity, crossreactivity, binding strength, kinetics and stochiometry of the interaction, a topic with significance in reagent development and antibody drug optimization; epitope mapping, with significance in basic molecular biology research and reagent development; enzyme induced polymerization or cleavage of proteins as well as post-translational modification, e.g phosphorylation, dephosphorylation, glycolysations, acetylation, methylation, ubiquitination, etc., of interacting proteins with significance in signaling pathway mapping; lead finding assay, e.g. ligand fishing using a bait protein or competition assay with significance in drug discovery; drug profiling assay, e.g. mapping protein complex formation in the cell upon application of the drug or other stress factors, with significance in biomarker discovery, validation and early drug profiling; higher throughput, direct analysis of protein-protein interactions-complexomics, interactomics or systems biology; any automated or higher throughput analysis to determine properties such as the binding kinetics, binding sites, identification or the stoichiometry of the components, either in vitro or in vivo; comparison of multiple cell lines, some of which may have supramolecular complexes which have been expressed, excited or perturbed, to differentiate presence of identified or unknown complex(es); any detection of phosphorylation/dephosphorylation sites, such as protein kinases, using these methods and measurement of protein transport throughout another entity, such as through a cell, or part of a cell.

The following specific embodiments are illustrative only for the various applications and do not limit the scope of the invention in any way:

EXPERIMENTAL

Mass Spectrometry—All the mass measurements have been performed on the macromizer instrument (Comet A G, Flamatt, Switzerland). The macromizer instrument is essentially a MALDI-TOF mass spectrometer designed to optimize ion transmission onto the small area of the cryodetector array. Every part of the instrument including all necessary ion optics, lasers and electronics were designed to enhance detection of high mass ions. For a more detailed instrumental description see Wenzel, et al. Anal. Chem. (2005).

Example 1

Figure 3:
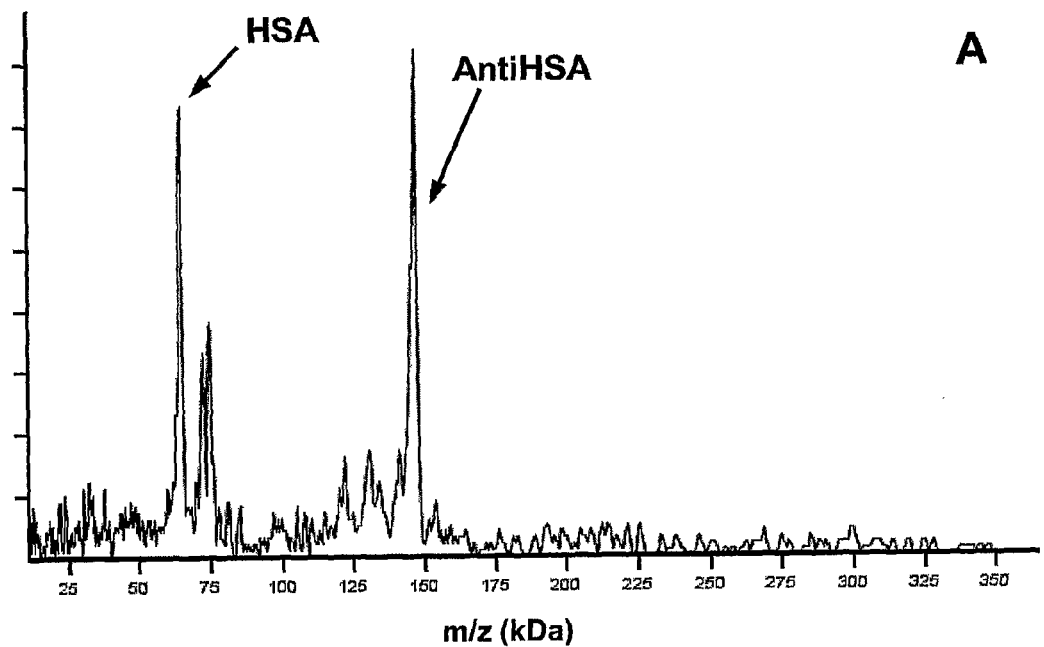
FIG. 3: Mass spectral results (Example 1) from a simple non-covalent antibody-antigen interaction analyzed under conventional conditions (FIG. 3A) und upon stabilization and subsequent analysis by high mass MALDI mass spectrometric techniques according to the invention (FIG. 3B).
Figure 3:
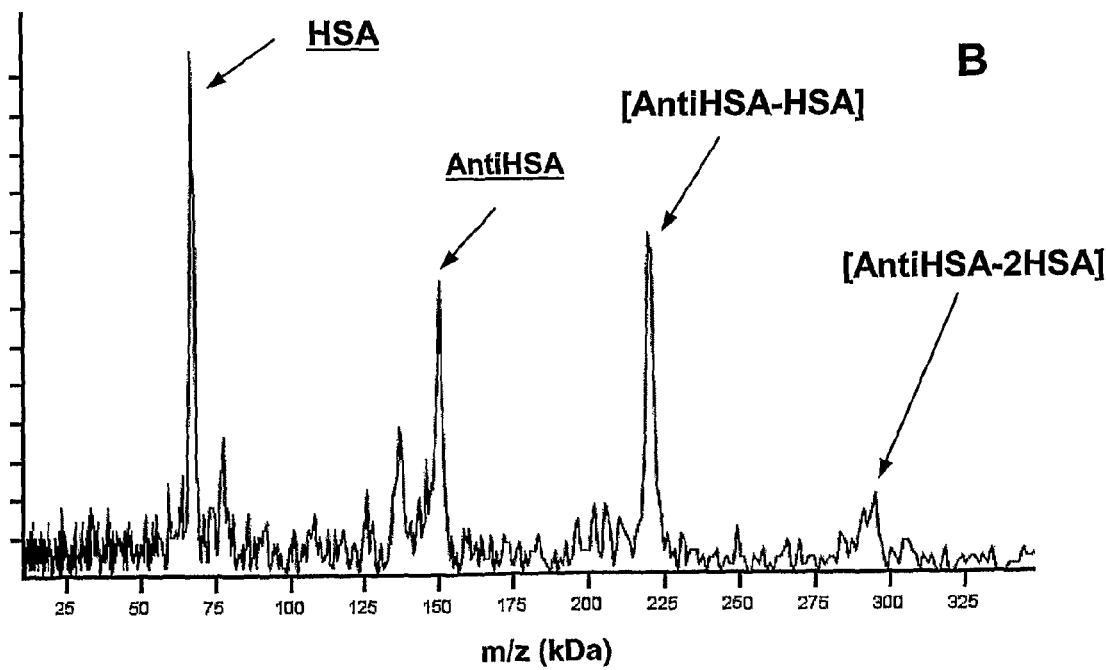

Mass Spectral Analysis of a Non-Covalent
(Antibody) Protein-Protein Interaction with and
without Crosslinking Stabilization Using MALDI This example demonstrates an antibody-antigen reaction under non-crosslinked conditions (FIG. 3A) and using crosslinking stabilization (FIG. 3B). The reactions involve 5 µL of 650 nM of Human Serum Albumin (HSA) reacting with 5 µL of 1 µM Anti-Human Serum Albumin (AntiHSA). FIG. 3B is the same sample as FIG. 3A however, includes the use of 1 µL of 1 mg/mL of crosslinking mixture allowing the easy identification of crosslinked peaks. Analysis was preformed using a macromizer (Comet AG; Flamatt, Switzerland) MALDI mass spectrometer under standard operating conditions. Samples were prepared using 1 µL of sample mixed with 1 µL of sinapic acid (10 mg/mL in 70% Acetonitrile:30% Water:0.1% Trifluoroacetic Acid) and spotting 1 µL using dried droplet technique.

Example 2

Figure 4:
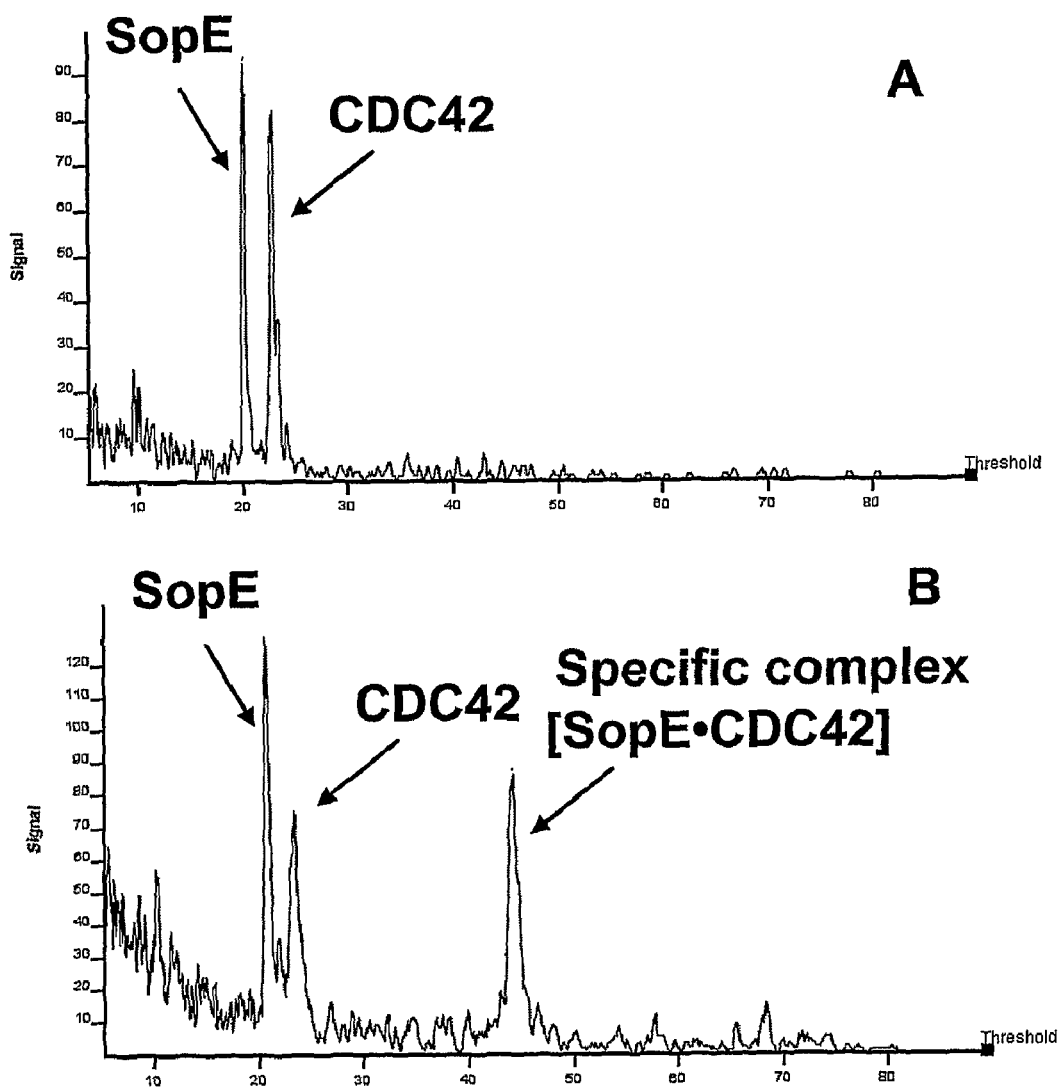
FIG. 4: Mass spectral results (Example 2) of the non-covalent interaction between two (non-antibody) proteins analyzed under conventional conditions (FIG. 4A) und upon stabilization and subsequent analysis by high mass MALDI mass spectrometric techniques according to the invention (FIG. 4B).

Mass Spectral Analysis of a Non-Covalent
(Non-Antibody) Protein-Protein Interaction with and
without Crosslinking Stabilization Using MALDI This example demonstrates a (non-antibody) protein-protein reaction between Cell Division Cycle 42 homolog (CDC42) and Salmonella outer protein E (SopE) under non-crosslinked conditions (FIG. 4A) and using crosslinking stabilization (FIG. 4B). The reactions involve 5 µL of 1 µM of SopE reacting with 5 µL of 1 µM CDC 42. FIG. 4B is the same sample as FIG. 4A however, includes the use of 1 µL of 1 mg/mL of crosslinking mixture allowing the easy identification of crosslinked peaks. Analysis was preformed using a macromizer (Comet AG; Flamatt, Switzerland) MALDI mass spectrometer under standard operating conditions. Samples were prepared using 1 µL of sample mixed with 1 µL of sinapic acid (10 mg/mL in 70% Acetonitrile:30% Water:0.1% Trifluoroacetic Acid) and spotting 1 µL using dried droplet technique.

Example 3

Figure 5:
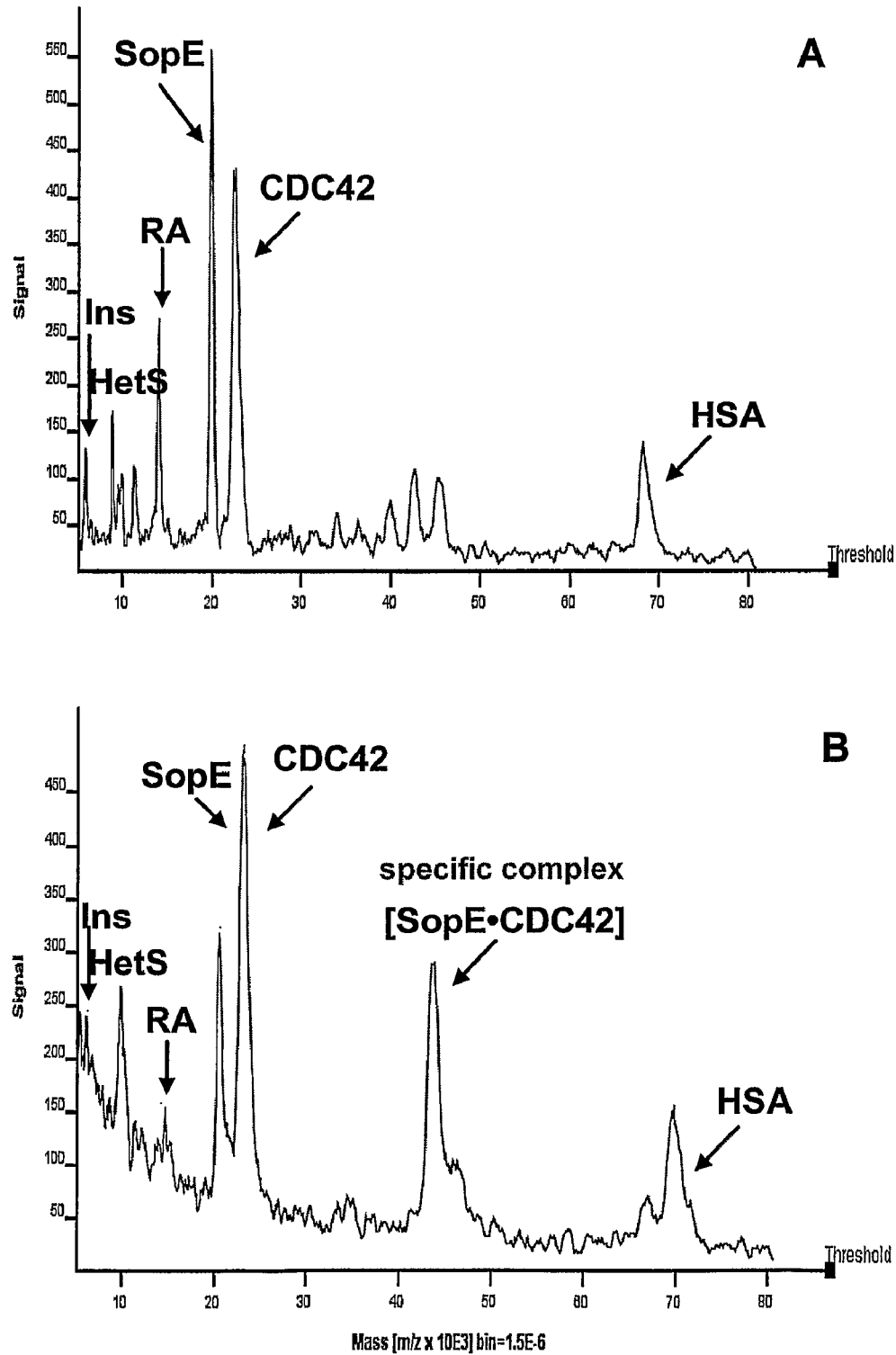
FIG. 5: Mass spectral results (Example 3) from a complex sample containing a non-covalent protein-protein interaction analyzed under conventional conditions (FIG. 4A) and upon stabilization using a crosslinking mixture and subsequent analysis by high mass MALDI mass spectrometric techniques according to the invention (FIG. 4B).

Mass Spectral Analysis of a Non-Covalent
Protein-Protein Interaction in a Complex Sample
Upon Crosslinking Stabilization Using MALDI This example demonstrates that it is possible to detect a specific protein complex within a multicomponent mixture of proteins. The reactions involve 6 different proteins (Insulin, HetS, RibonucleaseA, SopE, CDC42, HSA), 10 µL, 1 µM each (FIG. 5A). After cross-linking stabilization with 1 µL of 1 mg/mL crosslinking mixture the specific complex [CDC42•SopE] is detected (FIG. 5B). Analysis was performed using a macromizer (Comet AG; Flamatt, Switzerland) mass spectrometer under standard operating conditions. Samples were prepared using 1 µL of sample mixed with 1 µl of sinapic acid (10 mg/mL in 70% Acetonitrile:30% Water: 0.1% Trifluoroacetic Acid) and spotting 1 µL using dried droplet technique.

Example 4

Figure 6:
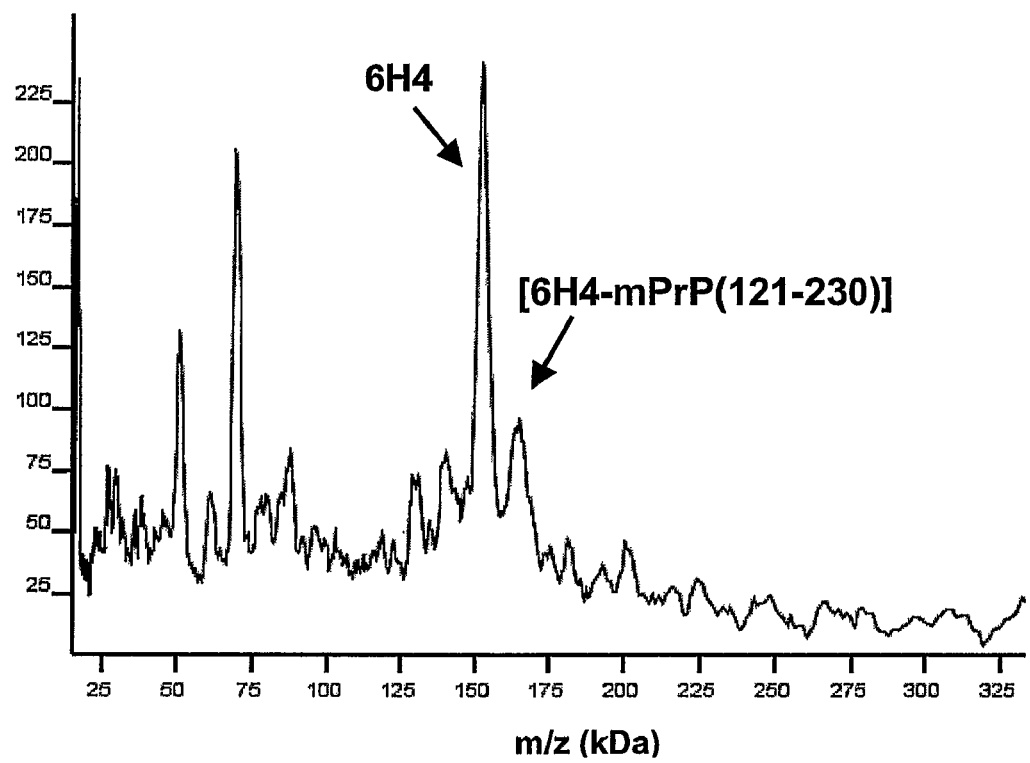
FIG. 6: Mass spectral results from a complex sample containing a non-covalent protein-protein interaction within human blood serum, which has been stabilized using a crosslinking mixture and measured by high mass MALDI mass spectrometric techniques according to the invention (Example 4).

Mass Spectral Analysis of a Non-Covalent
Protein-Protein Interaction within Human Blood
Serum Upon Crosslinking Stabilization Using
MALDI This example demonstrates an antibody-antigen reaction using crosslinking stabilization is specific when spike at 10 µM concentration within a sample of human blood serum (1:200 dilution). The reactions involve 5 µL of 650 nM of Anti-Prion Protein (6H4, Prionics; Switzerland) reacting with 5 µL of 1 pm/µL the globular subsection of mouse Prion Protein (mPrP(121-230)) and 1 µL of 2 mg/mL crosslinking mixture allowing the easy identification of crosslinked peaks (FIG. 6). Analysis was preformed using a macromizer (Comet A G; Flamatt, Switzerland) MALDI mass spectrometer under standard operating conditions. Samples were prepared using 1 µL of sample mixed with 1 µL of sinapic acid (10 mg/mL in 70% Acetonitrile:30% Water:0.1% Trifluoroacetic Acid) and spotting 1 µL using dried droplet technique.

Example 5

Figure 7:
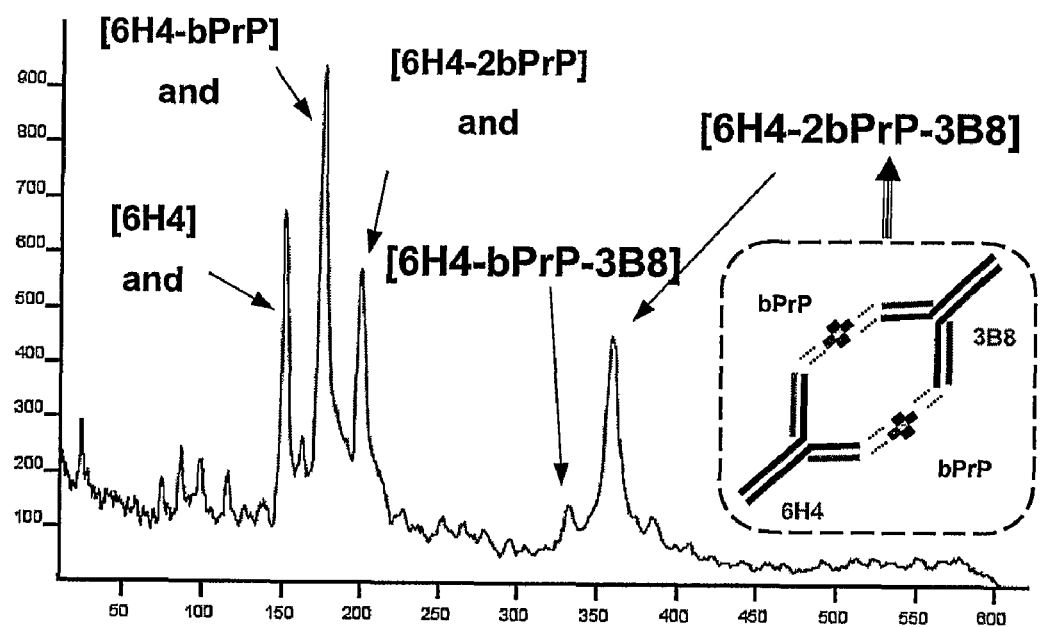
FIG. 7: Mass spectral results from a multiple component non-covalent complex, which has been stabilized using a crosslinking mixture and measured by high mass MALDI mass spectrometric techniques according to the invention (Example 5).

Mass Spectral Analysis of a Multiple Component
Non-Covalent Complex Upon Crosslinking
Stabilization Using MALDI This example demonstrates how multiple binding partners can be stabilized as one intact complex. The reactions involve 5 µL of 650 nM of Anti-Prion Protein (6H4, Prionics; Switzerland) reacting with 5 µL of 1 µM of bovine Prion Protein (bPrP) and 2.5 µL of 1.3 µM of Anti-Prion Protein (3B8, Roboscreen; Leipzig, Germany). The mixture was stabilized using 1 µL of 2 mg/mL crosslinking mixture allowing the easy identification of crosslinked peaks (FIG. 7). Analysis was preformed using a macromizer (Comet A G; Flamatt, Switzerland) MALDI mass spectrometer under standard operating conditions. Samples were prepared using 1 µL of sample mixed with 1 µL of sinapic acid (10 mg/mL in 70% Acetonitrile:30% Water:0.1% Trifloroacetic Acid) and spotting 1 µL using dried droplet technique.

Example 6

Kinetic Experiments

Figure 8:
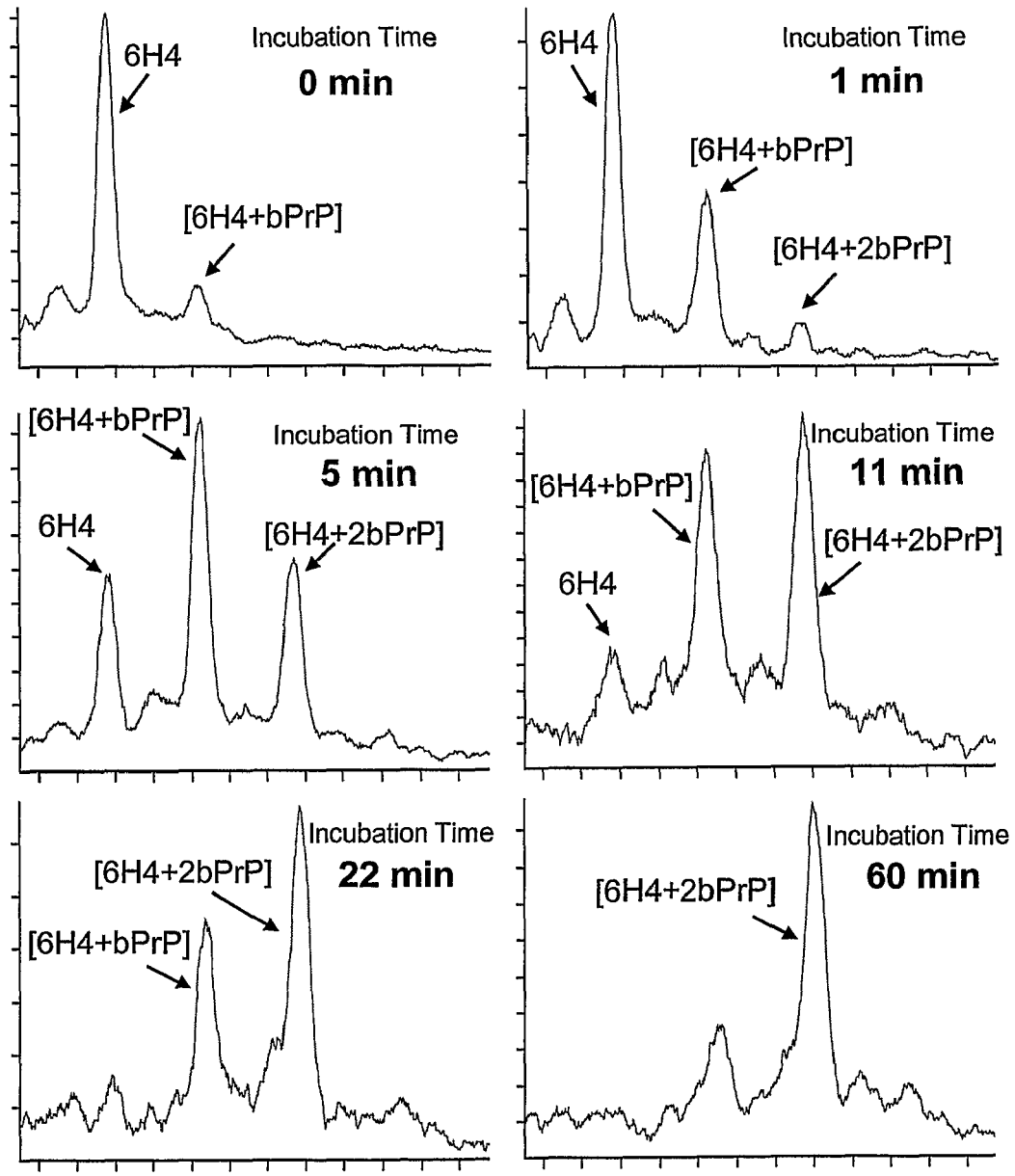
FIG. 8: Time course of mass spectral analysis of the formation of a multiply bound protein-protein complex (Example 6).
Figure 9:
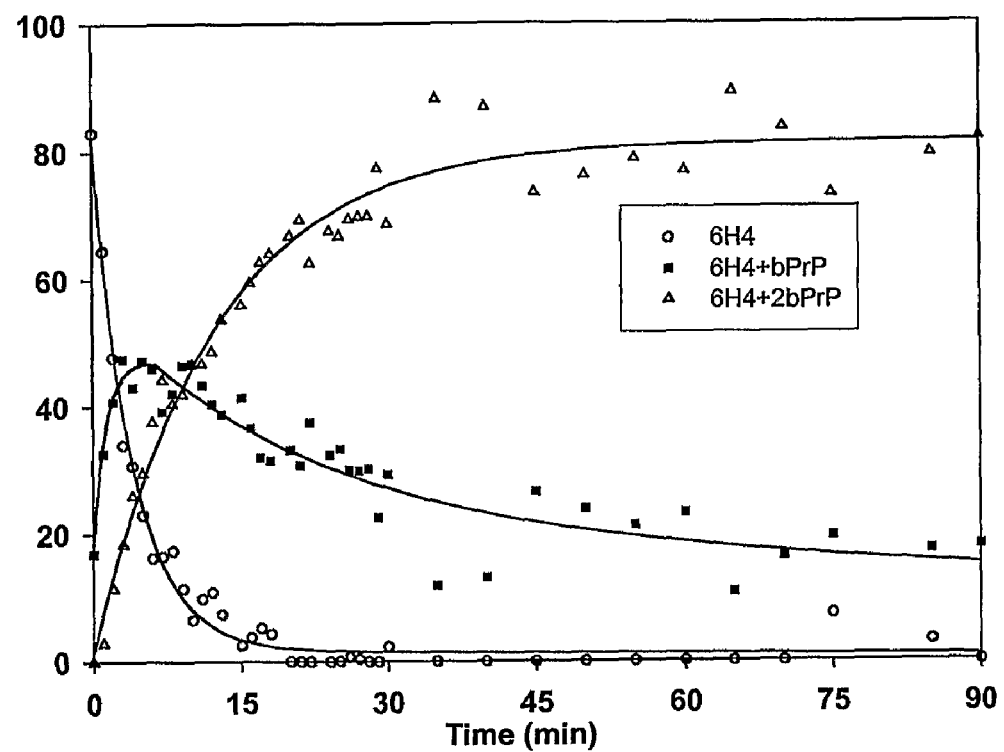
FIG. 9: Intensity of unbound, bound and multiply bound protein-protein interaction at different times during mass spectral analysis (Example 6).

A solution of monoclonal antibody against bPrP(23-230) (6H4, 600 nM, 300 µl, $H_2O$) was mixed at time 0 with a solution of bPrP(23-230) (1 µM, 300 µl, $H_2O$). After incubation, a 10 µl aliquot was drawn every minute from 1 to 30 minutes, then every 5 minutes from 30 minutes to 80 minutes and submitted for 10 minutes to the crosslinking reaction. Then the reaction was stopped by mixing 1 µl of the crosslinked sample with 1 µl of the matrix (sinapinic acid, 10 mg/ml in 7:3:1 acetonitrile:$H_2O$:0.1% TFA). For each incubation time, the reaction products were analyzed by macromizer mass spectrometry. The results are illustrated graphically in FIGS. 8 and 9. FIG. 8 shows that at t=o the major peak is the unbound 6H4 peak and after 5 minutes the major peak is the single binding of one 6H4 with one bPrP. After 60 minutes the reaction is complete with the major peak being one 6H4 bound with two bPrP molecules. FIG. 9 is a graphical illustration of the above mass spectral showing the intensity of unbound, bound and multiply bound protein-protein interaction occurring over different incubation times. The graph was obtained by calculating the ion intensity corresponding to each peak, subtracting the background ion intensity, and normalizing the intensity the peaks within each spectrum. These corrected, normalized ion intensities are then graphed over time.

The invention claimed is:

1. A method for analyzing intact ions of undigested, unfragmented supramolecular target-ligand-complexes using mass spectrometry comprising the steps of:
   a) contacting a non-covalently bonded, supramolecular target-ligand-complex with a crosslinking reagent to form a reaction mixture comprising a covalently stabilized supramolecular target-ligand-complex,
   b) mixing the reaction mixture comprising a covalently stabilized supramolecular target-ligand-complex, without separating, with a matrix solution to obtain a sample/matrix mixture, and
   c) analyzing the intact ions from the undigested, unfragmented covalently stabilized supramolecular target-ligand-complex in said sample/matrix mixture by MALDI mass spectrometry for high mass determination allowing intact ionization, detection and mass determination of molecules exceeding 300 kDa.

2. A method for detecting intact ions of an undigested, unfragmented supramolecular target-ligand-complex using MALDI mass spectrometry comprising:
   (a) obtaining a first sample comprising a non-covalently bonded supramolecular target-ligand-complex;
   (b) contacting said first sample with a crosslinking reagent to obtain a second sample comprising a covalently stabilized supramolecular target-ligand-complex;
   (c) without separating, mixing said second sample with a matrix solution to obtain a sample/matrix mixture;
   (d) depositing said sample/matrix solution on a substrate, thereby forming a homogeneous, thin layer;
   (e) illuminating the substrate with radiation from a laser whereby said covalently stabilized supramolecular target-ligand-complex in the sample/matrix mixture is desorbed and intact ions are generated; and
   (f) mass separating and detecting said intact ions of the undigested, unfragmented covalently stabilized supramolecular target-ligand-complex using MALDI mass spectrometry for high mass determination allowing intact ionization, detection and mass determination of molecules exceeding 300 kDa.

3. The method according to claim 1, wherein the supramolecular target-ligand-complex represents a complex of a target molecule with its binding ligand, wherein said target molecule is selected from proteins, polypeptides, glycopolypeptides, phosphopolypeptides, peptidoglycans, polysaccharides, peptidomimetics, lipids, carbohydrates, polynucleotides and other naturally occurring or synthetic macromolecules and said binding ligand is selected from a small molecule drug, peptide or polypeptide, nucleic acid or oligonucleotide, carbohydrate such as oligosaccharides, viral particles, proteins or any other organic derived compound.

4. The method according to claim 1, wherein the supramolecular target-ligand-complex to be analyzed is present in purified multicomponent samples or heterogeneous biological matrices.

5. The method according to claim 1, wherein a detector is used that is sensitive and non-saturating to high mass ions in the range of about 100 kDa to about 10 MDa selected from an Ion Conversion Dynode detector, an optically decoupled, amplified or specially coated electron multiplier or Microchannel Plate detector, and a Superconducting Tunnel Junction detector.

6. The method according to claim 1, wherein the crosslinking reagent is one or a mixture of crosslinking reagents selected from homo- and heteromultifunctional crosslinking agents comprising imidoesters, N-hydroxysuccinimide esters, maleimides, haloacetyls, pyridyl disulfides, hydrazides, carbodiimides, aryl azides, isocyanates, and vinyl sulfones.

7. The method according to claim 2, wherein the mass separating and detecting in step (f) is selected from the group consisting of: linear or reflectron time-of-flight, with linear and nonlinear fields, curved field reflectron; single or multiple quadrupole; single or multiple magnetic or electric sector; Fourier transform ion cyclotron resonance; ion trap, and a combination thereof.

8. The method according to claim 2, wherein a detector is used in step (f) that is sensitive and non-saturating to high mass ions and is selected from the group consisting of: a Superconducting Tunnel Junction (STJ) detector, an Ion Conversion Dynode detector, and an optically decoupled, amplified, or specially coated electron multiplier or Microchannel Plate detector.

9. The method according to claim 2, wherein in step (d) the sample/matrix mixture is deposited on a solid substrate in a two dimensional array and in step (f) mass separating and detecting is performed in a high throughput or automated fashion.

* * * * *